United States Patent
Schoenberger et al.

(10) Patent No.: US 9,045,288 B2
(45) Date of Patent: Jun. 2, 2015

(54) APPARATUS FOR THE HEATING OF PLASTICS MATERIAL PRE-FORMS WITH STERILE ROOM

(71) Applicant: Krones AG, Neutraubling (DE)

(72) Inventors: Wolfgang Schoenberger, Brennberg (DE); Gerhard Schwoed, Alteglogsheim (DE); Frank Winzinger, Freising (DE)

(73) Assignee: KRONES AG, Neutraubling (DE)

( * ) Notice: Subject to any disclaimer, the term of this patent is extended or adjusted under 35 U.S.C. 154(b) by 70 days.

(21) Appl. No.: 13/940,662

(22) Filed: Jul. 12, 2013

(65) Prior Publication Data
US 2014/0014465 A1   Jan. 16, 2014

(30) Foreign Application Priority Data
Jul. 13, 2012 (DE) .......... 10 2012 106 310

(51) Int. Cl.
| | |
|---|---|
| *B29C 49/46* | (2006.01) |
| *A61L 2/16* | (2006.01) |
| *B65G 49/00* | (2006.01) |
| *B29C 49/64* | (2006.01) |
| *B29C 49/42* | (2006.01) |

(52) U.S. Cl.
CPC .......... *B65G 49/00* (2013.01); *B29C 49/4205* (2013.01); *B29C 49/46* (2013.01); *B29C 49/6418* (2013.01); *B29C 2049/4679* (2013.01); *B29C 2049/4697* (2013.01); *B29C 2049/4294* (2013.01)

(58) Field of Classification Search
USPC ........ 264/520, 538; 198/343.1, 952; 432/239, 432/242; 422/304; 425/182, 525, 526, 541
See application file for complete search history.

(56) References Cited

U.S. PATENT DOCUMENTS

| | | | |
|---|---|---|---|
| 5,618,489 A * | 4/1997 | Weissmann | 264/530 |
| 6,562,281 B1 * | 5/2003 | Marchau et al. | 264/532 |

(Continued)

FOREIGN PATENT DOCUMENTS

| | | |
|---|---|---|
| DE | 2009047540 | 6/2011 |
| EP | 2329933 | 6/2011 |

(Continued)

OTHER PUBLICATIONS

German Search Report dated Mar. 11, 2013 issued in corresponding German Application No. 10 2012 106 310.9.

(Continued)

*Primary Examiner* — Douglas Hess
(74) *Attorney, Agent, or Firm* — Onello & Mello, LLP.

(57) ABSTRACT

In an apparatus for the heating of plastics material pre-forms with a conveying device which conveys the plastics material pre-forms along a pre-set conveying path, at least one heating device moves with the plastics material pre-forms arranged on the conveying device, wherein the heating device comprises a receiving room that receives the plastics material pre-forms and that surrounds the plastics material pre-forms during heating thereof. A holding device holds the plastics material pre-forms. The plastics material pre-forms are conveyed through a clean room, the clean room surrounding the conveying path of the plastics material pre-forms. A moving device introduces the plastics material pre-forms into the receiving room and removes plastics material pre-forms from the receiving room. At least one portion of the moving device is arranged exterior the clean room. A sealing device seals the clean room from an exterior environment.

17 Claims, 5 Drawing Sheets

(56) References Cited

U.S. PATENT DOCUMENTS

| | | | |
|---|---|---|---|
| 7,311,515 B2 * | 12/2007 | Netsu | 425/534 |
| 7,806,680 B2 * | 10/2010 | Adriansens et al. | 425/526 |
| 7,938,639 B2 * | 5/2011 | Adriansens et al. | 425/210 |
| 8,047,830 B2 * | 11/2011 | Kiefl | 425/182 |
| 8,083,512 B2 * | 12/2011 | Adriansens | 425/174.4 |
| 8,544,632 B2 * | 10/2013 | Gillet et al. | 198/465.2 |
| 8,632,325 B2 * | 1/2014 | Voth et al. | 425/3 |
| 8,708,681 B2 * | 4/2014 | Voth et al. | 425/73 |
| 8,771,584 B2 * | 7/2014 | Voth | 264/535 |
| 8,813,951 B2 * | 8/2014 | Forsthoevel et al. | 198/474.1 |
| 8,828,290 B2 * | 9/2014 | Voth et al. | 264/39 |
| 2011/0135288 A1 | 6/2011 | Winzinger et al. | |
| 2012/0038090 A1 | 2/2012 | Voth | |
| 2012/0070340 A1 | 3/2012 | Voth | |
| 2012/0269918 A1 | 10/2012 | Winzinger et al. | |
| 2013/0011807 A1 | 1/2013 | Winzinger et al. | |

FOREIGN PATENT DOCUMENTS

| | | |
|---|---|---|
| EP | 2412511 | 2/2012 |
| EP | 2431058 | 3/2012 |
| JP | 61261024 | 11/1986 |
| WO | 2011066886 | 6/2011 |
| WO | 2011066885 | 9/2011 |

OTHER PUBLICATIONS

Extended European Search Report dated Oct. 16, 2013, issued in corresponding European Application No. 13175061.4-1706.

* cited by examiner

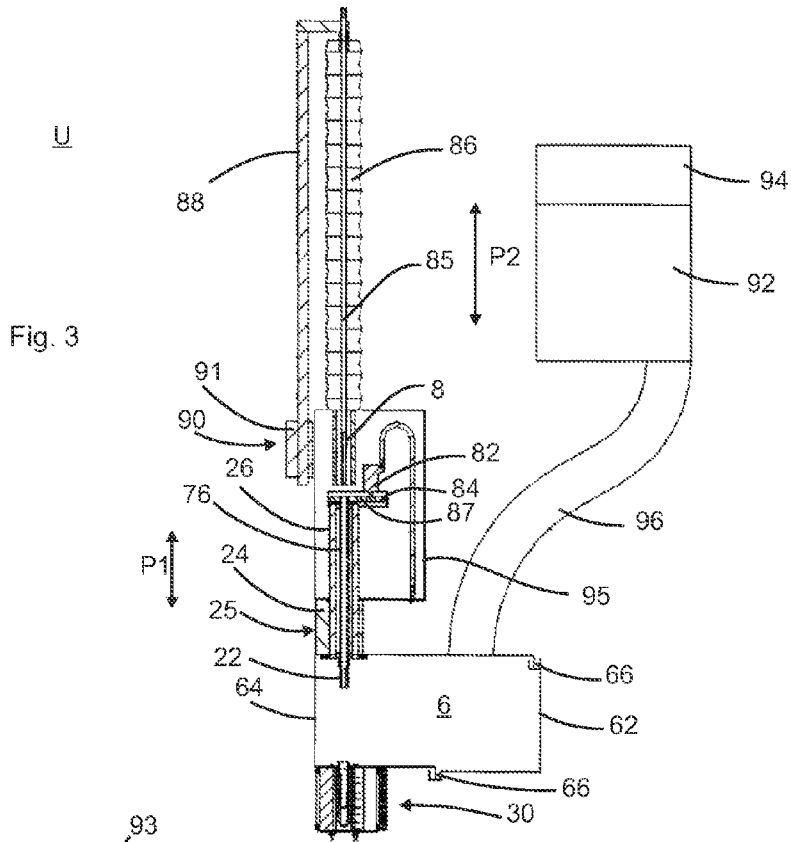
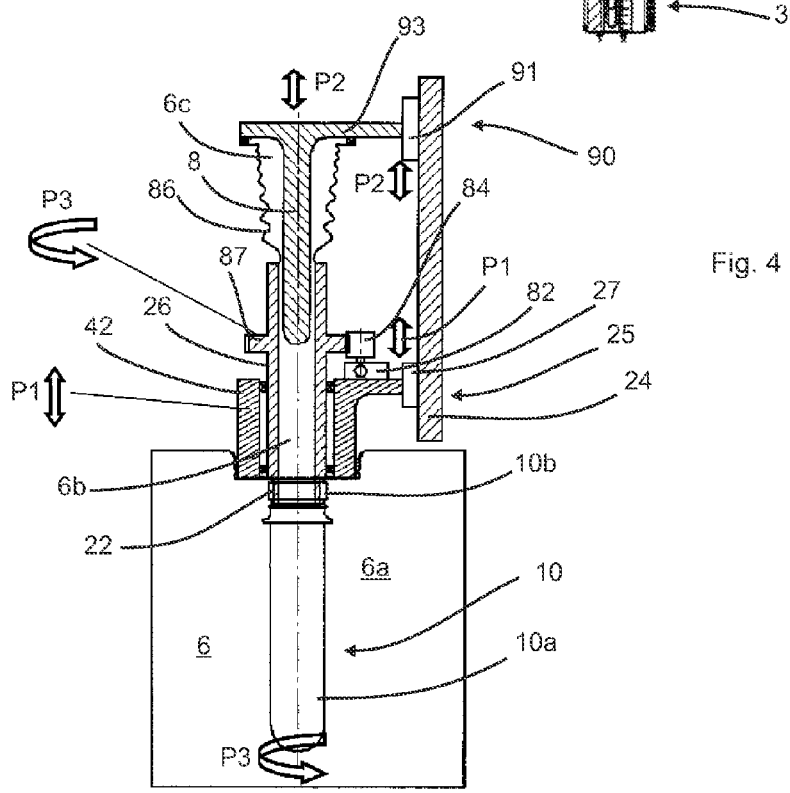

APPARATUS FOR THE HEATING OF PLASTICS MATERIAL PRE-FORMS WITH STERILE ROOM

RELATED APPLICATIONS

This application claims priority to German patent application number 10 2012 106 310.9 filed Jul. 13, 2012, the entire content of which is incorporated herein by reference, in its entirety.

BACKGROUND

Embodiments of the present inventive concepts relate to an apparatus for the heating of plastics material pre-forms. It is known conventionally for plastics material containers to be produced by plastics material pre-forms first being heated and then being shaped for example by a stretch blow moulding machine to form the plastics material containers.

For many beverages it is necessary to fill them under aseptic conditions. In this case it is known for plastics material pre-forms which are possibly contaminated by germs to be sterilized by a sterilization process upstream of the blow moulding machine. After that, the container can be transferred to the aseptic filling by way of an aseptic blow moulding machine. This sterilization of the plastics material pre-forms directly upstream of the blow moulding machine is subject to certain drawbacks, for example the complete removal of a sterilization agent before the shaping process, but in all events before the filling process.

SUMMARY

It is desirable that plastics material pre-forms which are already sterile and free of sterilization agents be supplied to this blow moulding machine.

Embodiments of the present inventive concepts therefore keep the plastics material pre-forms sterile at an earlier point in time and, in particular, to heat them when already in a sterile state.

An apparatus according to the inventive concepts for the heating of plastics material pre-forms can include a conveying device which conveys the plastics material pre-forms along a pre-set conveying path. In this case at least one heating device which moves with the plastics material pre-forms is arranged on this conveying device (and is therefore likewise conveyed along the conveying path), as well as a holding device for holding the plastics material pre-forms, the apparatus having a clean room through which the plastics material pre-forms are conveyed.

In some embodiments, this clean room surrounds the conveying path and, in addition, the heating device has a receiving room for receiving the plastics material pre-forms, which surrounds the plastics material pre-forms during the heating thereof at least locally.

According to the inventive concepts the apparatus can include a moving device in order to introduce the plastics material pre-forms into the receiving room and to remove them out of this receiving room, at least one component part of this moving device being arranged outside the clean room and a sealing device being provided which bounds the clean room off from a (non-sterile) environment. It is preferable for a sealing device to be provided which seals the movement of the moving device off from the clean room.

It is therefore proposed for the heating to be carried out inside a clean room. In this way, it is proposed according to the inventive concepts that the treatment room in which the plastics material pre-forms are heated should also be constructed and arranged in such a way that a sort of clean room is formed which is bounded off towards the outside from a non-sterile room or an environment and nevertheless allows the necessary process movements to be introduced without losing its sterility during this.

The receiving room is preferably a receiving room or a receiving cavity into which the plastics material pre-form is capable of being inserted and which preferably completely surrounds the plastics material pre-form in an inserted state in the peripheral direction thereof. It is advantageous for this receiving room to surround the plastics material pre-forms over their entire periphery in those regions of the plastics material pre-form which are situated below the carrier ring thereof and which are thus to be heated. It is preferable for a cross-section of the receiving room to be adapted to the geometry of the plastics material pre-form and preferably to have a circular cross-section. The receiving room preferably therefore has an opening by way of which the plastics material pre-form can be inserted. In addition, the receiving room can have a second opening through which a sterilization agent can be supplied to the receiving room or by way of which a sterilization agent can be removed.

It is advantageous for the apparatus to have a pressure stressing means which puts the aforesaid clean room under a pre-set over-pressure. In this way, it is possible to prevent contamination from penetrating into the clean room from an exterior environment in an undesired manner.

In the case of an advantageous design the conveying device has a rotatable carrier on which a plurality of heating devices are arranged. In this way, the plastics material pre-forms are advantageously conveyed along a circular conveying path during their heating.

It is advantageous for a drive of this conveying device to be arranged outside of the clean room. It is advantageous for the clean room to have an annular or toroidal profile, in which case in particular regions of the entire apparatus which are situated radially inside the conveying path of the plastics material pre-forms are also arranged outside the clean room. It is advantageous for at least one wall which bounds the clean room to be a component part of the carrier on which the heating device is arranged. It is advantageous for a plurality of heating devices to be arranged on the carrier.

In the case of a further advantageous design the apparatus can include a first wall and a second wall which bound the clean room off from an environment, and these walls can be movable relative to each other. In addition, it is advantageous for a sealing device to be provided which seals the movement of one wall off from the other wall. It is advantageous in this case for this sealing device to have a continuous channel which is preferably filled with a liquid. A component part of the wall which is movable relative to this channel can be configured to dip into this liquid.

In the case of a further advantageous design at least one heating element for heating the plastics material pre-forms is arranged outside the clean room. In this case it would be possible for this heating element to heat the plastics material pre-forms through a boundary of the clean room. This can preferably be an electrically operated heating element. In this way, it would be possible for the heating element itself to be arranged in a housing which is closed off and sealed off with respect to the clean room (and thus optionally also geometrically at least in part and preferably completely inside the clean room) and for the plastics material pre-forms to be heated through a wall of this housing. In addition, it would be possible for the heating element to have a microwave source and for these microwaves to be capable of passing through a wall of the aforesaid housing.

In the case of a further advantageous design a plurality of the heating elements and preferably all the heating elements are arranged outside the clean room. In the case of a further advantageous embodiment at least one heating element is provided in each case between two heating devices or between heating cavities into which the plastics material pre-forms are inserted. It is preferable for one or more heating elements to be arranged in each case between the individual holding devices for holding the plastics material pre-forms in the movement direction of the plastics material pre-forms.

It is pointed out that the herein described embodiments can be employed independently of the inventive concepts described herein, i.e. in particular independently of the arrangement of the moving device inside or outside the clean room. The Applicants reserve the right to apply a separate protection to designs of this type.

In the case of a further advantageous design the apparatus can include a rotary drive in order to rotate the plastics material pre-form about the longitudinal direction thereof at least for a time during its heating.

On account of this rotation of the plastics material pre-forms as uniform as possible a heating of the latter is achieved. In this way, it is advantageous for the plastics material pre-form to be capable of being inserted into the aforesaid heating device or a hollow space formed by the heating device and advantageously also to be capable of being rotated inside this hollow space, in particular about its own longitudinal direction.

In the case of a further advantageous design the rotary drive is arranged outside the clean room.

In some embodiments, the apparatus can include a mounting device for the rotatable mounting of the holding device. This mounting device can be arranged in this case in particular inside the clean room. In this case it is possible for the mounting to have a part which is rotationally fixed but, in particular, vertically displaceable, i.e. displaceable in the longitudinal direction of the plastics material pre-forms, and also one or more mounting bodies which are used for the rotatable mounting of the holding device. It is advantageous for the aforesaid drive for the rotary movement also to be arranged on the rotationally fixed mounting part.

The drive can comprise for example an electric motor, but it would also be possible for this drive to be implemented by way of a set of teeth. In the case of a further advantageous embodiment a moving device in the form of a motor, and in particular a linear motor, is provided which inserts the plastics material pre-forms into the heating device. In this way, a motor, and in particular a linear motor, also advantageously moves the mounting unit with the aforesaid holding device for holding the plastics material pre-forms. It is advantageous for the holding device to be a holding mandrel which is inserted into the plastics material pre-forms in order to hold them. In this case this holding mandrel can be provided in its peripheral direction with clamping means which press against the inner wall of the plastics material pre-form and thus provide for a secure hold of the plastics material pre-form.

In the case of a further advantageous design the apparatus can include a rod-like body which is capable of being inserted into the inner space of the plastics material pre-forms in order to heat them. With this design a duplex heating method is proposed, in which the plastics material pre-form is preferably heated at the same time from the inside by way of the aforesaid rod-like body and from the outside by way of the heating device or a heating bush. It is advantageous in this case for this heating system to be arranged on a rotary slider. The plastics material pre-forms are preferably first supplied to the latter, are transferred to a collet chuck or a clamping element and then immersed in the heating device.

In some embodiments, the rod-like body or the heating lance also can also be inserted parallel to the latter into the plastics material pre-form. In this embodiment, the plastics material pre-form stays in this heating system for a specified heating duration; it can be set in continuous rotation in order to ensure a uniform heating around the periphery of the plastics material pre-form. After the heating process it is advantageous for the plastics material pre-form to be drawn out of the heating device again and preferably to be transferred to a shaping device.

In some embodiments, an STIR (selected transmission infrared) process is employed.

In the case of the designs described here the holding of the plastics material pre-form, in particular, is also described in greater detail. The necessary reciprocating movements of the holding device and/or of the rod-like body and also the introduction of the rotational movement and the sterile sealing of these reciprocating and rotational movements off from each other as well as the sterilization boundaries of the clean room are described in greater detail here. It is advantageous for the holding device to be mounted in a vertically displaceable loading head (i.e. the mounting device described above). In this way, the latter can receive the plastics material pre-form by way of its aperture and can dip it further (for example downwards) into the clean room or the heating device respectively. The above-mentioned rod-like body, which in this case also is advantageously mounted so as to be vertically displaceable for example in a linear direction, can likewise be inserted into the plastics material pre-form.

It is advantageous for a moving device for moving this rod-like body to be arranged outside the clean room. In this case a sealing device can likewise again be provided, which seals this relative movement off from the clean room. It is advantageous for this sealing device to be a folding bellows.

In the case of a further advantageous design this moving device is an electric motor and, in particular, a linear motor. It would also be possible, however, for other drives to be used, such as for example pneumatic or hydraulic drives. In addition, a sealing device can also be provided which seals off the rotational movement of the plastics material pre-form.

In the case of a further advantageous design the holding device is arranged on a carrier which is designed at least locally in the form of a hollow body. In this case it is advantageous for the rod-like body mentioned above to be capable of being passed through this carrier or this hollow body respectively. In other words, an advantageously vertically displaceable and mounted heating lance can dip into the plastics material pre-form by way of a hollow-drilled holding device. In the case of this design it is preferably possible for a rotational movement to be introduced into the holding device by means of a rotary drive which is preferably arranged in a fixed manner on this holding device or a carrier. It is advantageous in this case for the rotating parts of this mounting device to be sealed off by way of aseptic bearings.

In this case it is preferable for at least one portion of the rod-like body also to be capable of being inserted into the clean room.

In the case of a further advantageous design the rotary drive for the plastics material pre-form is arranged outside the clean room. It is advantageous for a sealing device also to be provided which seals off this rotational movement. In some embodiments, this is a sealing device which can also seal off a linear movement, for example a reciprocating movement. In this way, it would be possible for this sealing device likewise to be a surge tank or an hydraulic seal respectively.

The heating device can be in particular an infrared furnace or even a STIR furnace. It would also be possible, however, for the heating device to be a microwave heating device, i.e. the heating device has at least one microwave generation device (such as in particular a magneton) as well as also a resonator inside which the plastics material pre-forms are heated. In the case of this design each heating device advantageously forms a resonator of this type for heating the plastics material pre-forms.

In the case of a further advantageous design the apparatus can include a sterilization device for sterilizing the plastics material pre-forms and/or for sterilizing inner regions of the clean room. In this case, as mentioned, it is possible for the plastics material pre-forms themselves to be sterilized, but it would also be possible for a CIP sterilization or cleaning unit to be provided. In this case the sterilization device can be designed in such a way that it acts upon the desired regions with a radiation, for example an electron radiation or even an UV radiation. It would also, however, be possible for a flowable medium (for example hydrogen peroxide or peracetic acid) to be used for the sterilization or cleaning.

It is preferable for the sterilization device to have a stressing device which acts upon at least one wall situated inside the clean room or upon a boundary wall of the clean room with a flowable sterilization agent.

It is advantageous for the heating device to have, as well as a first opening through which the plastics material pre-form is introduced into the receiving room, a second opening which, in particular, is used for sterilization or cleaning purposes, for example in order to supply a sterilization agent to the heating device or to remove it from the latter again.

In some embodiments, the stressing device comprises a supply device for supplying the flowable sterilization agent, this supply device having a channel which extends through at least one wall of the clean room or, on the other hand, through at least one region of the holding device. In the case of this design the holding mandrel or the holding device can be designed for example in the form of a hollow body. In this case a sterilization agent could also be introduced into the plastics material pre-forms by way of the holding device. In this case it would also be possible, in particular, for this sterilization agent to be introduced during the heating of the plastics material pre-forms.

In the case of a further advantageous design sloping faces which permit a purposeful removal of a sterilization agent can be provided in the interior of the clean room.

The present inventive concepts further relate to a method of heating plastics material pre-forms, in which the plastics material pre-forms are conveyed along a pre-set conveying path and are heated during this conveying. In addition, for the purpose of this heating the plastics material pre-forms are introduced in each case into heating devices associated with these plastics material pre-forms, these heating devices likewise moving along the conveying path. In addition, the plastics material pre-forms are conveyed at least locally through a clean room during their heating, in which case this clean room is bounded off from an environment by means of at least one wall.

According to the inventive concepts a moving device introduces the plastics material pre-forms into a receiving room or a receiving cavity of this heating device and this moving device is arranged at least in part outside the clean room.

It is advantageous for the conveying path of the plastics material pre-forms to be a circular conveying path.

In addition, it is advantageous for at least one region of this clean room and/or the heating device to be acted upon at least for a time with a cleaning and/or sterilization agent for the purpose of cleaning.

In addition, it is advantageous for the plastics material pre-forms to be rotated, in particular about the longitudinal direction thereof, at least for a time during their heating.

In an aspect, an apparatus for the heating of plastics material pre-forms with a conveying device which conveys the plastics material pre-forms along a pre-set conveying path, comprises: at least one heating device that moves with the plastics material pre-forms arranged on the conveying device, wherein the heating device comprises a receiving room that receives the plastics material pre-forms and that surrounds the plastics material pre-forms during heating thereof; a holding device that holds the plastics material pre-forms; a clean room through which the plastics material pre-forms are conveyed, the clean room surrounding the conveying path of the plastics material pre-forms; a moving device that introduces the plastics material pre-forms into the receiving room and that removes plastics material pre-forms from the receiving room, wherein at least one portion of the moving device is arranged exterior the clean room; and a sealing device that seals the clean room from an exterior environment.

In some embodiments, the conveying device comprises a rotatable carrier on which a plurality of heating devices are arranged.

In some embodiments, the comprises a first wall and a second wall which bound the clean room from an exterior environment, and wherein the walls are movable relative to each other.

In some embodiments, the apparatus comprises a rotary drive that rotates the plastics material pre-forms for a time period during heating thereof.

In some embodiments, the apparatus further comprises a heating element that heats the plastics material pre-forms arranged exterior the clean room.

In some embodiments, the apparatus further comprises a mounting device for the rotatable mounting of the holding device.

In some embodiments, the apparatus further comprises a rod-like body insertable into the inner space of the plastics material pre-forms in order to heat the plastics material pre-forms.

In some embodiments, the apparatus further comprises a moving device for moving the rod-like body positioned exterior the clean room.

In some embodiments, the holding device is arranged on a carrier which is at least partially hollow.

In some embodiments, a rod-like body is capable of being passed through the hollow body.

In some embodiments, the rotary drive is positioned outside the clean room.

In some embodiments, the apparatus further comprises a sterilization device that sterilizes the plastics material pre-forms or that sterilizes inner regions of the clean room.

In some embodiments, the sterilization device includes a stressing device which acts upon at least one wall situated inside the clean room or upon a boundary wall of the clean room with a flowable sterilization agent.

In some embodiments, the stressing device comprises a supply device that supplies the flowable sterilization agent, wherein the supply device comprises a channel that extends through at least one wall of the clean room or through at least one region of the holding device.

In an aspect, a method of heating plastics material pre-forms comprises: conveying plastics material pre-forms along a pre-set conveying path and heating the plastics material preforms during the conveying using a heating device; wherein heating the plastics material pre-forms comprises introducing them into associated heating devices that likewise move along the conveying path, wherein the plastics material pre-forms are conveyed at least locally through a clean room during their heating, wherein the clean room is bounded off from an external environment by at least one wall, and wherein a moving device introduces the plastics material pre-forms into a receiving room of the heating device and wherein the moving device is arranged at least partially external the clean room.

BRIEF DESCRIPTION OF THE DRAWINGS

Further advantages and embodiments are evident from the accompanying drawings. In the drawings

FIG. 3 is an illustration of an apparatus for heating plastics material pre-forms;

FIG. 4 is an illustration of a moving device for the introduction of the plastics material pre-forms into the heating cavities;

DETAILED DESCRIPTION OF EMBODIMENTS

Figure 1:
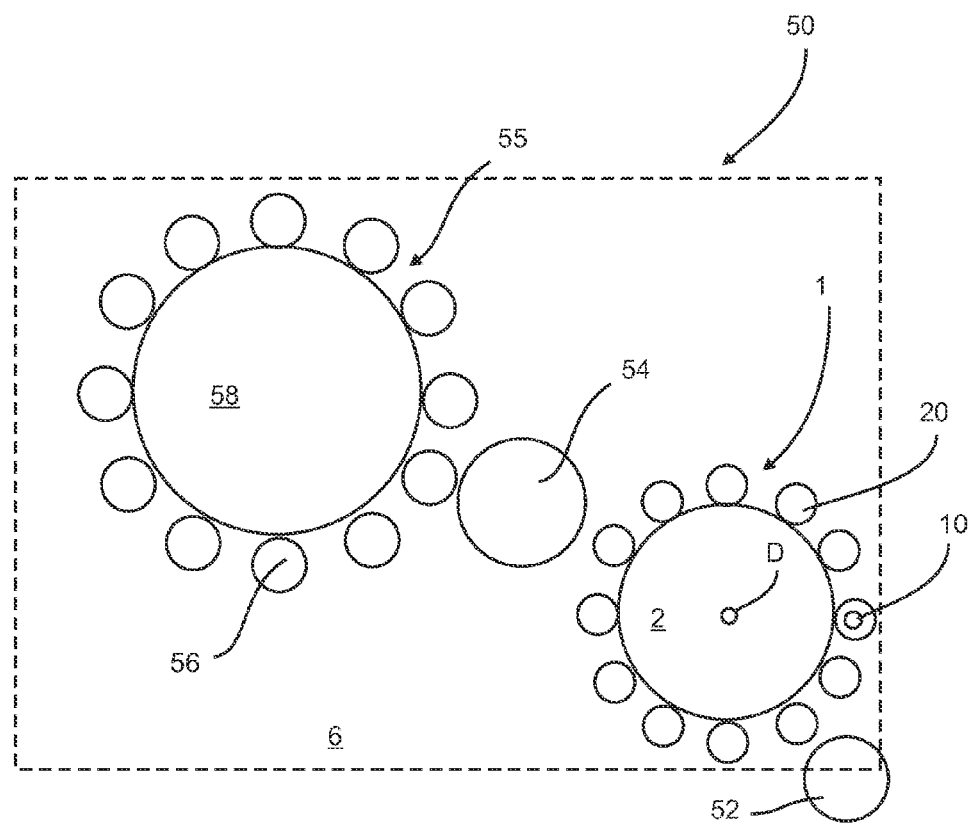
FIG. 1 is a diagrammatic illustration of an arrangement for the production of containers.

Exemplary embodiments in accordance with principles of inventive concepts will now be described more fully with reference to the accompanying drawings, in which exemplary embodiments are shown. Exemplary embodiments in accordance with principles of inventive concepts may, however, be embodied in many different forms and should not be construed as being limited to the embodiments set forth herein; rather, these embodiments are provided so that this disclosure will be thorough and complete, and will fully convey the concept of exemplary embodiments to those of ordinary skill in the art. Like reference numerals in the drawings denote like elements, and thus their description may not be repeated.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of exemplary embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Exemplary embodiments in accordance with principles of inventive concepts are described herein with reference to cross-sectional illustrations that are schematic illustrations of idealized embodiments (and intermediate structures) of exemplary embodiments. As such, variations from the shapes of the illustrations as a result, for example, of manufacturing techniques and/or tolerances, are to be expected. Thus, exemplary embodiments in accordance with principles of inventive concepts should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of exemplary embodiments.

Unless otherwise defined, all terms (including technical and scientific terms) used herein have the same meaning as commonly understood by one of ordinary skill in the art to which exemplary embodiments in accordance with principles of inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a diagrammatic illustration of a plant 50 for the treatment of containers. In this case plastics material pre-forms 10 (only one shown) are supplied by way of a supply device 52 to a heating apparatus designated 1 as a whole. This heating apparatus has a carrier 2 which is rotatable in this case about an axis of rotation D and on which a plurality of heating devices or stations 20 respectively are arranged. After they have been heated, the plastics material pre-forms are transferred by way of a transfer star wheel 54 to a shaping device designated 55 as a whole for shaping plastics material pre-forms into plastics material containers. This shaping device also has a rotatable carrier 58 and a plurality of shaping stations 56 arranged on it. In this case the shaping device 55 is advantageously a blow moulding machine, and in particular a stretch blow moulding machine.

Both the heating device 1 and the shaping device 55 are arranged in this case in a clean room 6 illustrated only diagrammatically. This means that the plastics material pre-forms are already conveyed inside this clean room 6 during their heating. In addition, it would be possible for the plant to have for example sterilization devices which sterilize the heating devices 20 or even the plastics material pre-forms 10 themselves. The supply device 52 can likewise in this case be arranged at least in part in the clean room.

Figure 2:
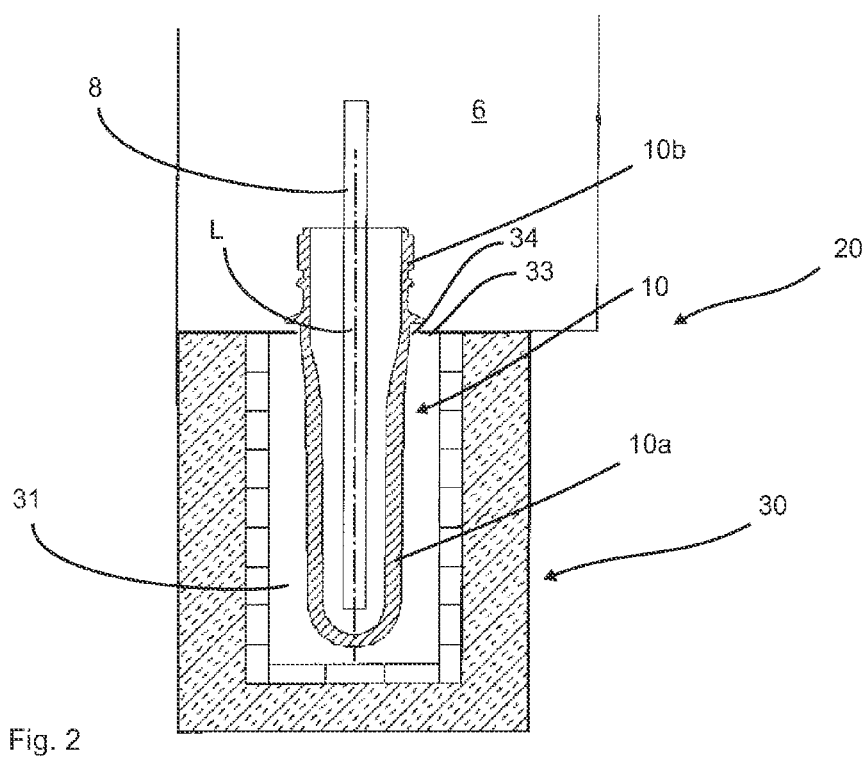
FIG. 2 is a detailed view of a heating device for heating plastics material pre-forms.

FIG. 2 is a partial illustration of a heating device 20. This heating device has a heating cavity which is designated 30 as a whole and which forms a hollow space 31 into which the plastics material pre-form 10 is inserted. This plastics material pre-form 10 has in this case a main body 10a as well as a threaded region 10b. This threaded region does not arrive in the heating cavity 30 during the heating. It is possible in fact for screening devices 33 to be provided which prevent heating of the thread. The reference number 34 designates an opening in the heating cavity 30 by way of which the plastics material pre-form 10 can be supplied to the heating cavity 30. Each screening device 33 can be designed in this case in the form of a plate which in turn has an opening through which the plastics material pre-form 10 is capable of being passed.

The reference number 8 designates a rod-like body which is likewise inserted into the plastics material pre-forms 10 in this case during the heating. This rod-like body 8 also heats the plastics material pre-forms 10 at an internal region thereof. In this way, a uniform heating of the plastics material pre-forms 10 is possible. The reference letter L designates the longitudinal direction of the plastics material pre-forms which coincides in this case with the longitudinal direction and movement direction of the rod-like body.

In this case too, the reference number 6 again designates the clean room, inside which the plastics material pre-forms are heated. Since the heating cavity 30 is likewise closed off here, the hollow space 31 also forms part of the clean room 6.

FIG. 3 shows a further illustration of the apparatus according to the inventive concepts. In this case the heating cavity 30 and the clean room 6 adjoining it are again evident. This clean room 6 is advantageously made annular here and has a first wall 62 and a second wall 64. This second wall 64 is arranged so as to be movable or rotatable respectively in this case and the wall 62 is arranged so as to be stationary. The reference numbers 66 refer to sealing devices which seal off the movement between the walls. These sealing devices 66 can in this case, as mentioned above, be designed in each case in the form of a so-called surge tank, in which case a portion of the wall 64 engages in a channel formed by the wall 62. An over-pressure preferably prevails in the sterile room 6 in this case in order to prevent the penetration of germs. In addition, a blower 92 is provided in order to supply the sterile room 6 by way of a line 96. The reference number 94 designates a filter device, such as for example a HEPA filter.

The reference number 24 designates a stator of a linear motor 25 which is used to move the plastics material pre-forms into the heating cavity 30 (as well as for moving them out of the heating cavity). The associated movable part or secondary part, i.e. the slider, is designated with the reference number 26 here. This slider 26 is designed in this case in the form of a hollow shaft, so that the rod-like body 8 can also be introduced into the plastics material pre-form through this hollow shaft.

The reference number 22 designates a holding device for holding the plastics material pre-forms 10. This holding device is preferably designed in this case in the form of a holding mandrel which engages in the apertures of the plastics material pre-forms and thus holds them from the inside. Holding devices would also be possible, however, which grip the plastics material pre-forms from the outside. It would also be possible, however, for the rod-like body 8 which is capable of being inserted into the plastics material pre-forms to be arranged directly on the holding device. In this way, the holding device could be designed in the form of an elongate mandrel which has a portion which is capable of being inserted into the plastics material pre-forms as well as a portion which holds the plastics material pre-forms.

The reference number 90 designates a second electric motor drive and the reference number 91 designates the stator thereof. The reference number 88 designates the slider of this second drive device 90. This slider 88 in this case moves a carrier rod 85 likewise in the direction P2. The reference number 86 designates a folding bellows which seals this movement of the carrier 85 in the direction P2 off from the environment U. Instead of the linear motors it is also possible for other types of drive to be used, such as for example pneumatic or hydraulic drives or even other electric motors. The reference number 82 designates a drive, in particular an electric motor, which produces a rotational movement of the plastics material pre-form about the longitudinal axis thereof, i.e. the longitudinal direction L. This drive 82 can have in this case an output gear 84 which drives a gearwheel 87 arranged on a carrier 76. The holding device 22 for holding the plastics material pre-forms 10 is in turn arranged on this carrier 76 and thus jointly rotates.

In this way, in the case of the designs shown here, a duplex heating method, as mentioned above, is presented, in which heating is carried out simultaneously from the inside, or interior regions, by way of a heating lance and from the outside, or exterior regions, by way of the heating cavity or heating bush. It is preferable for this heating system to be arranged on a rotary slider, in which case the plastics material pre-forms are supplied to the latter, are transferred to a holding device 22 for holding and are then immersed in the heating cavity. The rod-like body 8 is also inserted parallel thereto into the plastics material pre-forms 10. The plastics material pre-form 10 now stays in this system for a certain heating duration and is preferably set in continuous rotation in this case, in order to ensure a uniform heating around the periphery of the plastics material pre-form. After the heating process the plastics material pre-form is drawn out of the heating cavity 30 again and is transferred to the shaping device 55.

FIG. 4 illustrates this manner of operation and, in particular, the reciprocating movements provided for this. In this case too, the holding device 22 for holding the plastics material pre-forms is again provided. It is arranged on a carrier 26 which, as indicated by the arrow P3, is rotatable with the plastics material pre-form 10. The reference 10a designates a main body of the plastics material pre-form 10 and the reference 10b an aperture area into which the holding device 22 is inserted.

It will be seen that the carrier 26 is hollow-drilled and is arranged on a loading head 42 which is vertically displaceable and which in this case acts as a mounting device at the same time. The reference number 25 designates a first moving device which is provided for moving this loading head or carrier 42. This moving device is designed in this case in the form of a linear motor and has a stator 24 on which a slider 27 is movable in the direction of the arrow P1, i.e. upwards and downwards in this case.

The rotational movement of the plastics material pre-form is implemented in this case by a drive 82 which drives an output gear 84 which in turn drives a gearwheel 87 arranged on the carrier 26. In this way, in the case of this design too, the drive 82 for implementing the rotational movement is arranged outside the clean room 6. The clean room 6 extends in this case from the lower region 6a by way of the hollow space 6b of the carrier 26 into the room 6c, which is surrounded by the sealing device 86. The sealing device 86 is designed in this case in the form of a folding bellows. In this way, the clean room 6 is formed in this case from the regions 6a, 6b and 6c which are connected to one another.

In addition, the rod-like body 8 (which in reality can be longer than shown in FIG. 4) can be moved along the direction P2, i.e. upwards and downwards. A moving device designated 90 as a whole is also provided for this purpose. This moving device 90 is likewise designed in this case in the form of a linear motor and has on the one hand the carrier 24 (in the form of a stator) again and on the other hand the slider 91 which moves in the direction P2. The reference number 93 designates the carrier on which the rod-like body 8 is arranged.

Figure 5:
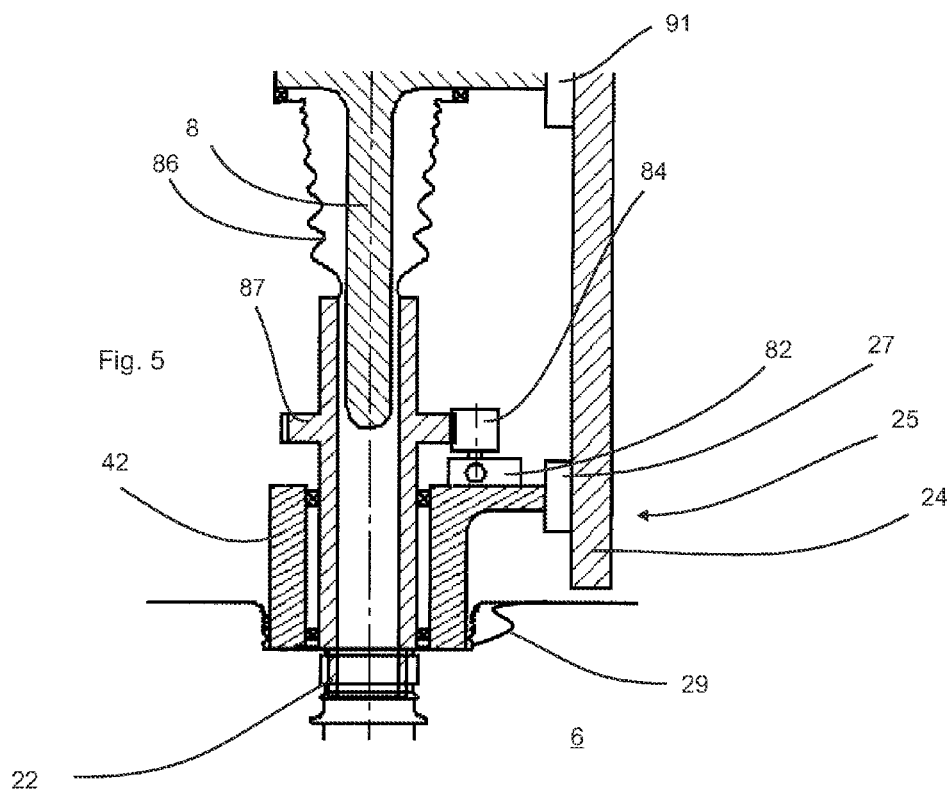
FIG. 5 is a detailed illustration of the illustration shown in FIG. 4.

FIG. 5 is an enlarged illustration of the apparatus shown in FIG. 4. It will be seen in this case that the drive 82 is arranged on the carrier 42 or the loading head respectively. In addition, a further sealing device or a further folding bellows 29 respectively is provided which seals the relative movement of the carrier 42 or the loading head respectively in the direction P1 off from the portion 6 of the clean room situated below. The mounting device 42 for mounting the carrier 26 is preferably designed in the form of an aseptic mounting in this case. This folding bellows can be arranged for example on the one hand on the carrier or the mounting device 42 and on the other hand on a wall of the clean room (6) in order to seal off the transition between the regions 6a and 6b of the clean room (cf. FIG. 4) in this way.

Figure 6:
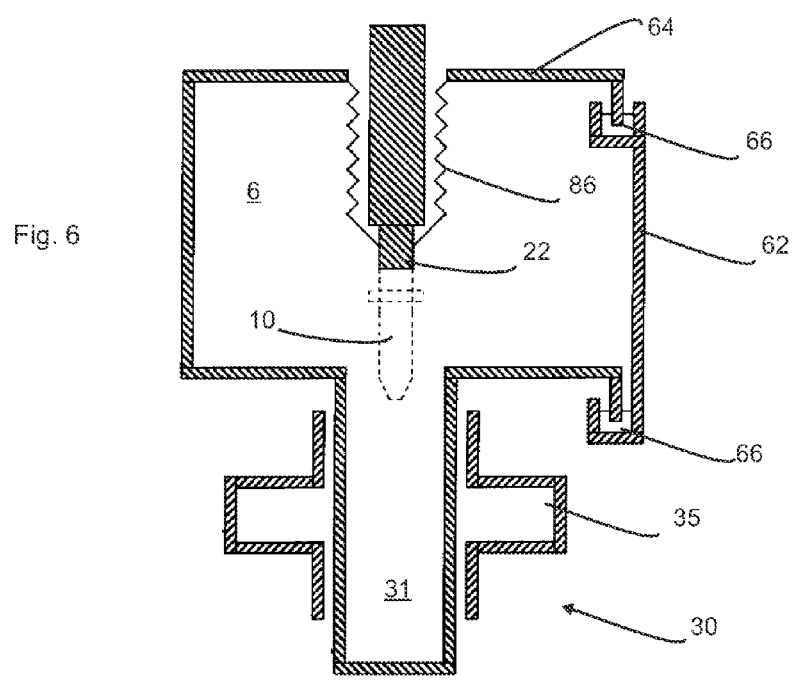
FIG. 6 is a further illustration of an apparatus according to the inventive concepts for the heating of plastics material pre-forms.

FIG. 6 shows a further design of an apparatus according to the inventive concepts. In this case the walls 62 and 64 movable with respect to each other are again provided, as well as also the sealing device 66 designed in the form of a surge tank. A folding bellows 86 is also provided again here in order to seal off the movement of the holding device 22 on which the plastics material pre-form 10 is arranged. The reference number 30 refers in this case again to the heating cavity as a whole, the receiving room 31 for heating the plastics material pre-form being directly connected in this case to the clean room 6. The reference number 35 again refers to a heating device. A problem with this design, however, is a rotation of the plastics material pre-form, which rotation is not permitted by the folding bellows 86.

Figure 7:
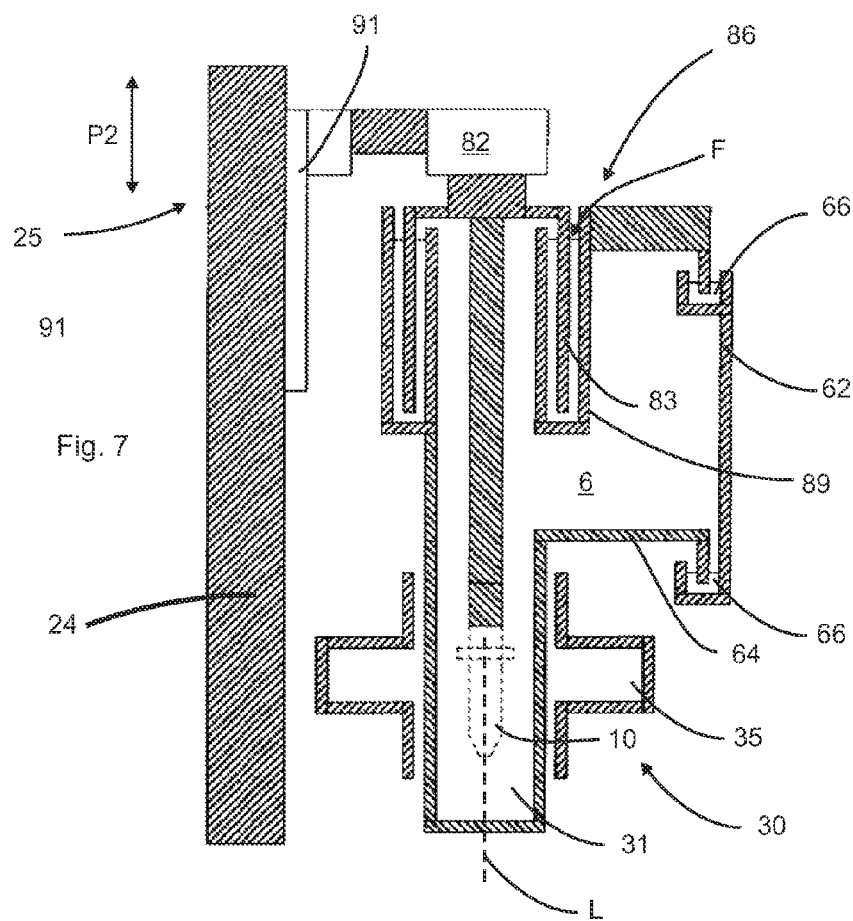
FIG. 7 is a further embodiment according to the inventive concepts of an apparatus for the heating of plastics material pre-forms.

FIG. 7 shows an embodiment in which a relative rotation of the plastics material pre-form 10 is also permitted. In this case too, the receiving room 31, into which the plastics material pre-form 10 dips, is provided. The sealing device 86 provided is not, however, in the form of a folding bellows but in the form of a surge tank which extends about the longitudinal axis L of the plastics material pre-form and thus also about the axis of rotation thereof. This surge tank has in this case a receiving channel 89 which, as mentioned, is made circular and continuous, as well as a blade 83 which dips into a liquid F in this channel 89. The reference number 91 in turn designates the slider which performs the movement in the direction of the arrow P2, i.e. the reciprocating movement. The reference number 82 in turn designates the drive for implementing the rotational movement of the plastics material pre-form 10. On account of the relatively great height of the sealing device or the surge tank 86 respectively it is also possible in this case to perform relatively large reciprocating movements whilst maintaining the clean room 6.

As mentioned in this case, an apparatus of this type for heating plastics material pre-forms can have a plurality of heating stations, as shown in FIG. 7. In this case, in particular, each of these heating stations can also have a sealing device 86 in each case in the form of a surge tank. These surge tanks can be fed in this case by way of a central distribution with one another and the provision can be made that these individual sealing devices or surge tanks 86 also have in each case the same filling level by means of an overflow connection.

In addition, a sensor device can be provided which controls a water level of the liquid F inside the channel 89.

In some embodiments, some or all of the sealing devices or seals mentioned here which form a clean room boundary can also be rubber seals.

Figure 8:
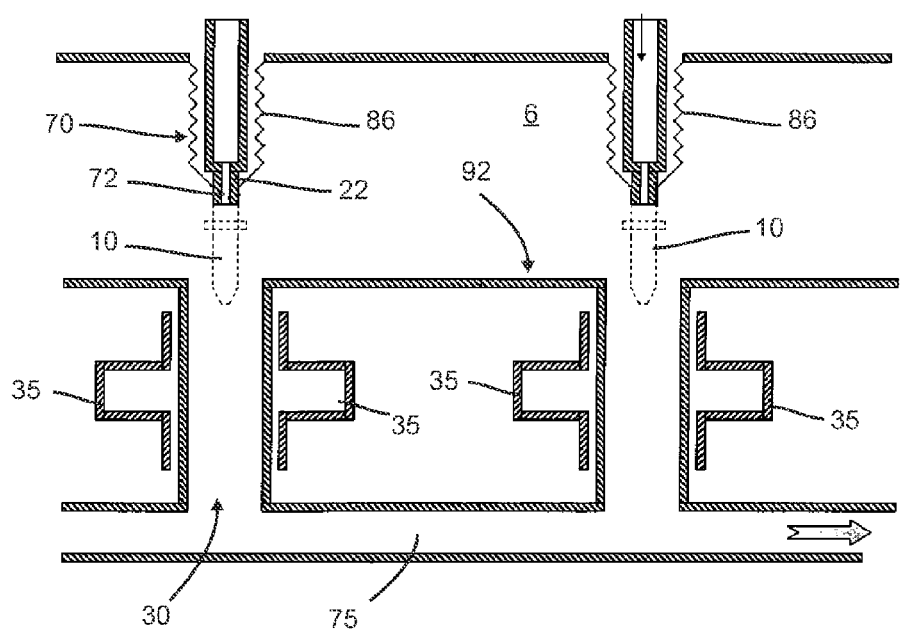
FIG. 8 is an illustration to explain a cleaning procedure.

FIG. 8 shows an illustration of the apparatus according to the inventive concepts in a cleaning state. In this case too, the individual holding devices 22 are again provided on which the plastics material pre-forms 10 are arranged. The heating elements 35 are arranged here in screens 92 in each case. As mentioned above, the heating devices 30 can be STIR heating devices, but also for example microwave heating devices.

The reference number 70 designates in this case a sterilization or cleaning device, this function also being performed in this case by the holding device 22. For this purpose the holding device 22 has in this case a channel 72 by way of which a cleaning agent can be supplied. In the case of the embodiment shown in FIG. 8 the individual heating devices are screened off from the clean room 6 by the housing 92 and, in this way, the heating devices 35 are situated outside the clean room.

By means of the sterilization device 70 it is possible for an inner wall of the heating cavity 30 to be capable of having a cleaning agent, for example a CIP medium, flow continuously around it. In addition, it is possible for the plastics material pre-form itself to be sterilized by means of the channel 72.

Figure 9:
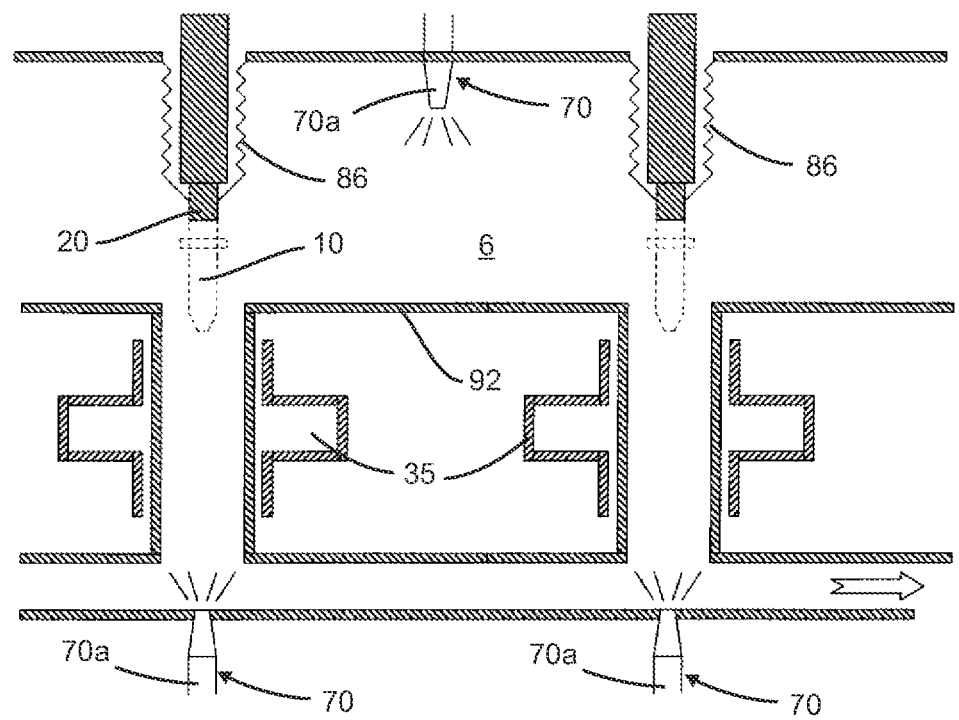
FIG. 9 is a further illustration to explain a cleaning procedure.

FIG. 9 is a further illustration of an apparatus according to the inventive concepts. In this case too, sterilization devices are again provided, but in contrast to the design shown in FIG. 8 these are accommodated in the walls bounding the clean room 6. In this design as well, the heating devices 35 are arranged outside the clean room in housings 92 (preferably closed off in each case).

The reference number 75 designates a removal line by way of which sterilization agent can be removed from the plant. In this case a pump can be provided which is used for removing this sterilization agent. The references 70a refer to stressing devices or nozzles which apply the sterilization agent to regions situated inside the clean room 6.

Figure 10:
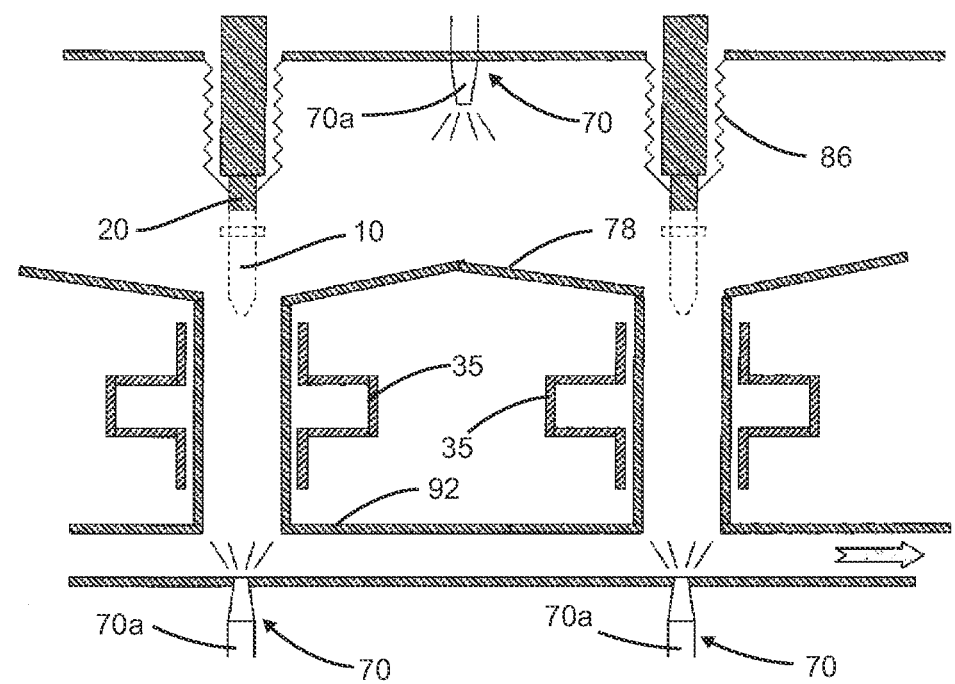
FIG. 10 is a further illustration to explain a cleaning procedure.

In the case of the embodiment shown in FIG. 10 the housings 92 are designed with sloping faces 78, so that sterilization agent which arrives at these sloping faces can flow downwards more easily.

The Applicants reserve the right to claim all of the features disclosed in the application documents as being essential to the inventive concepts either individually or in combination, insofar as they are novel as compared with the prior art.

What is claimed is:

1. An apparatus for the heating of plastics material pre-forms with a conveying device which conveys the plastics material pre-forms along a pre-set conveying path, comprising:
at least one heating device that moves with the plastics material pre-forms arranged on the conveying device, wherein the heating device comprises a receiving room that receives the plastics material pre-forms and that surrounds the plastics material pre-forms during heating thereof, wherein the receiving room includes a receiving cavity into which the plastics material pre-forms are capable of being inserted and which surrounds the plastics material pre-forms in an inserted state in a peripheral direction thereof, and wherein the receiving room has a first opening by way of which the plastics material pre-forms are inserted, and a second opening through which a sterilization agent can be supplied to the receiving room or from which a sterilization agent can be removed from the receiving room;
a holding device that holds the plastics material pre-forms;
a clean room through which the plastics material pre-forms are conveyed, the clean room surrounding the conveying path of the plastics material pre-forms;
a moving device that introduces the plastics material pre-forms into the receiving room and that removes plastics material pre-forms from the receiving room, wherein at least one portion of the moving device is arranged exterior the clean room; and
a sealing device that seals the clean room from an exterior environment.

2. An apparatus according to claim 1, wherein the conveying device comprises a rotatable carrier on which a plurality of heating devices are arranged.

3. An apparatus according to claim 2, wherein the apparatus comprises a first wall and a second wall which bound the clean room from an exterior environment, and wherein the walls are movable relative to each other.

4. An apparatus according to claim 1, wherein the apparatus comprises a rotary drive that rotates the plastics material pre-forms for a time period during heating thereof.

5. An apparatus according to claim 4, further comprising a heating element that heats the plastics material pre-forms arranged exterior the clean room.

6. An apparatus according to claim 5, further comprising a mounting device for the rotatable mounting of the holding device.

7. An apparatus according to claim 4, wherein the rotary drive is positioned outside the clean room.

8. An apparatus according to claim 1, further comprising a rod-like body insertable into the inner space of the plastics material pre-forms in order to heat the plastics material pre-forms.

9. An apparatus according to claim 8, further comprising a moving device for moving the rod-like body positioned exterior the clean room.

10. An apparatus according to claim 1, wherein the holding device is arranged on a carrier which is at least partially hollow.

11. An apparatus according to claim 10, wherein a rod-like body is capable of being passed through the hollow body.

12. An apparatus according to claim 1, further comprising a sterilization device that sterilizes the plastics material pre-forms or that sterilizes inner regions of the clean room.

13. An apparatus according to claim 12, wherein the sterilization device includes a stressing device which acts upon at least one wall situated inside the clean room or upon a boundary wall of the clean room with a flowable sterilization agent.

14. An apparatus according to claim 12, wherein the stressing device comprises a supply device that supplies the flowable sterilization agent, wherein the supply device comprises a channel that extends through at least one wall of the clean room or through at least one region of the holding device.

15. A method of heating plastics material pre-forms, comprising:
conveying plastics material pre-forms along a pre-set conveying path and heating the plastics material preforms during the conveying using a heating device;
wherein heating the plastics material pre-forms comprises introducing the plastics material pre-forms into associated heating devices that likewise move along the conveying path, wherein a rod-like body is insertable into an inner space of the plastics material pre-forms in order to heat the plastics material pre-forms,
wherein the plastics material pre-forms are conveyed at least locally through a clean room during their heating, wherein the clean room is bounded off from an external environment by at least one wall, and wherein a moving device introduces the plastics material pre-forms into a receiving room of the heating device and wherein the moving device is arranged at least partially external the clean room.

16. An apparatus for the heating of plastics material pre-forms with a conveying device which conveys the plastics material pre-forms along a pre-set conveying path, comprising:
at least one heating device that moves with the plastics material pre-forms arranged on the conveying device, wherein the heating device comprises a receiving room that receives the plastics material pre-forms and that surrounds the plastics material pre-forms during heating thereof;
a holding device that holds the plastics material pre-forms;
a rod-like body insertable into an inner space of the plastics material pre-forms in order to heat the plastics material pre-forms;
a clean room through which the plastics material pre-forms are conveyed, the clean room surrounding the conveying path of the plastics material pre-forms;
a moving device that introduces the plastics material pre-forms into the receiving room and that removes plastics material pre-forms from the receiving room, wherein at least one portion of the moving device is arranged exterior the clean room; and
a sealing device that seals the clean room from an exterior environment.

17. An apparatus for the heating of plastics material pre-forms with a conveying device which conveys the plastics material pre-forms along a pre-set conveying path, comprising:
at least one heating device that moves with the plastics material pre-forms arranged on the conveying device, wherein the heating device comprises a receiving room that receives the plastics material pre-forms and that surrounds the plastics material pre-forms during heating thereof;
a holding device that holds the plastics material pre-forms;
a clean room through which the plastics material pre-forms are conveyed, the clean room surrounding the conveying path of the plastics material pre-forms;
a moving device that introduces the plastics material pre-forms into the receiving room and that removes plastics material pre-forms from the receiving room, wherein at least one portion of the moving device is arranged exterior the clean room;

a sealing device that seals the clean room from an exterior environment; and a sterilization device that sterilizes the plastics material pre-forms or that sterilizes inner regions of the clean room.

* * * * *